United States Patent [19]
Peterson et al.

[11] Patent Number: 6,078,837
[45] Date of Patent: Jun. 20, 2000

[54] METHOD AND APPARATUS FOR TREATMENT OF FIBRILLATION

[75] Inventors: David K. L. Peterson, Santa Clarita, Calif.; Michael J. Link, St. Paul, Minn.

[73] Assignee: Medtronic, Inc., Minneapolis, Minn.

[21] Appl. No.: 09/238,862

[22] Filed: Jan. 27, 1999

[51] Int. Cl.$^7$ ....................................................... A61N 1/362
[52] U.S. Cl. ................................................................ 607/14
[58] Field of Search ................................... 607/4, 5, 9, 14

[56] References Cited

U.S. PATENT DOCUMENTS

| | | |
|---|---|---|
| 3,937,226 | 2/1976 | Funke . |
| 4,266,551 | 5/1981 | Stein . |
| 4,275,737 | 6/1981 | Thompson et al. . |
| 4,340,062 | 7/1982 | Thompson et al. . |
| 4,406,286 | 9/1983 | Stein . |
| 4,407,288 | 10/1983 | Langer et al. . |
| 4,649,931 | 3/1987 | Beck . |
| 4,830,006 | 5/1989 | Haluska et al. . |
| 4,958,632 | 9/1990 | Duggan . |
| 5,022,395 | 6/1991 | Russie . |
| 5,174,289 | 12/1992 | Cohen ........................................ 607/9 |
| 5,379,776 | 1/1995 | Murphy et al. . |
| 5,464,432 | 11/1995 | Infinger et al. . |
| 5,549,641 | 8/1996 | Ayers et al. . |
| 5,620,468 | 4/1997 | Mongeon et al. . |
| 5,674,251 | 10/1997 | Combs et al. . |
| 5,720,295 | 2/1998 | Greenhut et al. . |
| 5,755,736 | 5/1998 | Gillberg et al. . |
| 5,843,141 | 12/1998 | Bischoff et al. . |
| 5,871,511 | 2/1999 | Bolz et al. ................................ 607/14 |
| 5,873,896 | 2/1999 | Ideker ....................................... 607/14 |

FOREIGN PATENT DOCUMENTS 9218198  10/1992  WIPO .

OTHER PUBLICATIONS

"Regional Control of Atrial Fibrillation by Rapid Pacing in Conscious Dogs", by Allessie et al, published in Circulation, vol. 84, No. 4, Oct. 1991, pp. 1689–1697.

"Automatic Tachycardia Recognition", by Arzbaecher et al, published in Pace, vol. 7, May–Jun. 1984, part II, pp. 541–547.

Prevention of Atrial Tachyarrhythmias Related to Advanced Interatrial Block by Permanent Atrial Resynchronization, by Daubert et al, Pace, vol. 14, P. 648, 1991.

*Primary Examiner*—William E. Kamm
*Attorney, Agent, or Firm*—Reed A. Duthler; Harold R. Patton

[57] ABSTRACT

A cardiac stimulator and a method of its use. The stimulator includes a lead system carrying a stimulation electrodes adapted to be located at multiple sites adjacent tissue of a patient's heart and is provided with stimulation pulse generators coupled to deliver stimulation pulses to the stimulation electrodes. The stimulator further includes depolarization sensors responsive to depolarizations of cardiac tissues at the tissue sites and, responsive to sensed depolarizations and stimulation pulses delivered to said sites by said stimulation electrodes determines exitable gaps of tissue at the sites. The stimulator calculates stimulus pulse delivery times at variable delivery times within the determined exitable gaps at the tissue sites to cause convergence of depolarization cycles at the tissue sites over a series of delivered stimulation pulses and delivers stimulation pulses to the stimulation electrodes at the calculated variable delivery times.

16 Claims, 11 Drawing Sheets

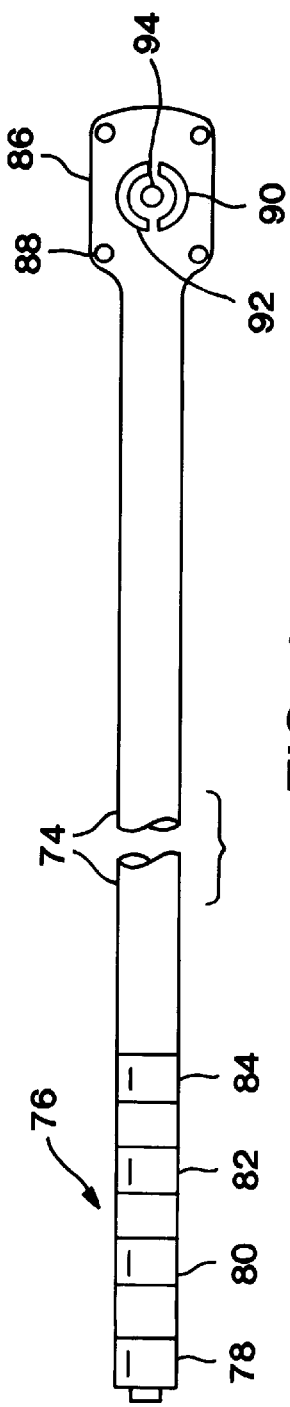
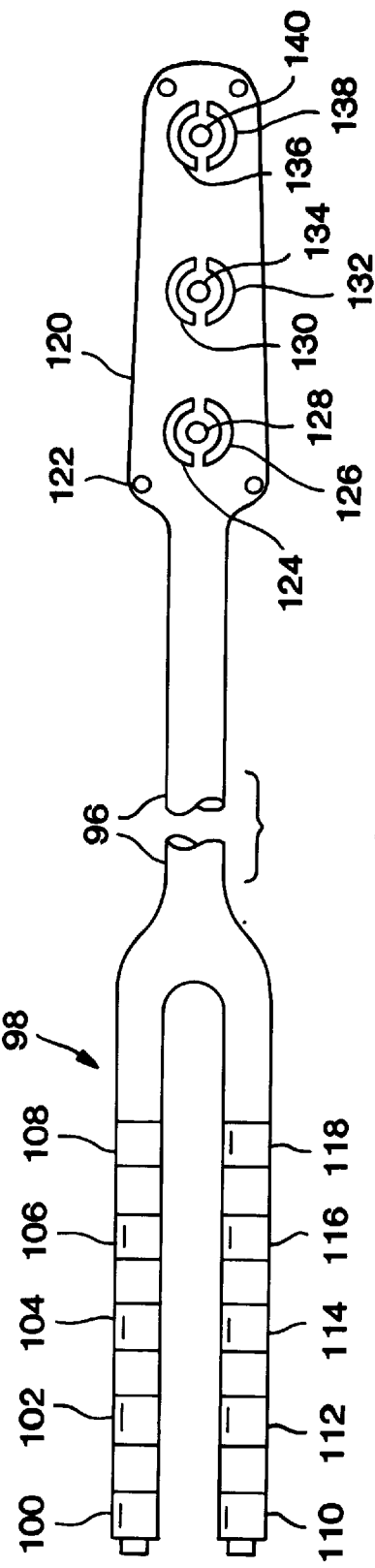

METHOD AND APPARATUS FOR TREATMENT OF FIBRILLATION

BACKGROUND OF THE INVENTION

This invention relates generally to implantable stimulators and, more specifically, to implantable pacemakers, cardioverters and defibrillators.

Over the years, numerous methods have been proposed for pacing the heart in an attempt to interrupt tachycardias. These include such pacing modalities as overdrive pacing, burst pacing, autodecremental overdrive pacing, and others. These pacing modalities have been formulated to interrupt aberrant reentrant conduction which may lead to sustained tachycardias in one or more chambers of the heart.

It has been proposed that tachycardias could be prevented or interrupted by the use of multi-site cardiac pacing. One early example of multi-site cardiac pacing to terminate or prevent tachyarrhythmia is disclosed in U.S. Pat. No. 3,937,226 issued to Funke. In this device, a number of small surface area pacing electrodes are provided, each coupled to a separate output circuit and amplifier. The disclosed device is equivalent to five or more separate cardiac pacemaker output circuits of conventional design, all adapted to be triggered to pace simultaneously at various locations around the heart. It is hypothesized that by stimulating simultaneously at locations spread around the heart, synchronous with a sensed QRS complex, arrhythmias could be prevented by producing a more nearly simultaneous depolarization of cardiac tissues.

In contrast, fibrillation has generally been treated by means of high energy shocks, which, in the context of implantable anti-arrhythmia devices, are applied by means of large surface area electrodes, including an electrode on or in the chamber to be defibrillated. The high energy level is employed in order to simultaneously depolarize the bulk of the heart chamber to be defibrillated, which will include tissues in all stages of the depolarization-repolarization cycle at the time the pulse is delivered.

In the context of atrial fibrillation, a proposed pacemaker/defibrillator is disclosed in PCT Application No. US92/02829, Publication No. WO 92/18198 by Adams et al, incorporated herein by reference in its entirety. In this reference careful synchronization of the high voltage atrial defibrillation pulse to the ventricles to avoid induction of ventricular tachycardia or fibrillation is discussed. Delivery of an atrial defibrillation pulse at an inappropriate time may induce ventricular arrhythmias, including ventricular fibrillation.

Use of pacing pulses delivered at multiple sites within the atria to prevent the occurrence of atrial tachyarrhythmias including atrial flutter, which may in some cases progress to atrial fibrillation, has been investigated. For example, the article "Prevention of Atrial Tachyarrhythmias Related to Advanced Interatrial Block by Permanent Atrial Resynchronization, by Daubert et al, Pace, Vol.14, P. 648, 1991, discloses the use of synchronized pacing pulses delivered to the right and left atria to prevent onset of atrial tachyarrhythmias.

Recently, the theoretical possibility of employing pacing level pulses (e.g. less than 0.05 joules) to terminate fibrillation has been explored. For example, in the recent article "Regional Control of Atrial Fibrillation by Rapid Pacing in Conscious Dogs", by Allessie et al, published in Circulation, Volume 84, No. 4, October 1991, pages 1689–1697, the ability of pacing pulses to capture a small area of fibrillating atrial tissue, if applied during a specified time interval synchronized to the sensed depolarization waveform at the pacing electrode site has been demonstrated. However, the depolarization wavefront created by such pulses does not propagate through the entire chamber, due to the varying polarization states of the tissue surrounding the stimulation site.

In an effort to capture a greater percentage of the heart during fibrillation, it has been proposed to use high frequency pacing delivered at multiple sites on or in the fibrillating heart chambers. These therapies are based on the understanding that capture will occur at one or more sites where a delivered pacing pulse is appropriately timed and that the delivery of high frequency pacing pulses thereafter and/or delivery of pacing pulses at multiple sites will serve to gradually enlarge the volume of heart tissue being paced, ultimately terminating fibrillation. Such pacing level therapies are disclosed in U.S. Pat. No. 5,674,251, issued to Combs et al. and U.S. Pat. No. 5,620,468, issued to Mongeon et al.

SUMMARY OF THE INVENTION

The present invention is directed toward providing an improved method and apparatus for terminating fibrillation of a chamber of the heart using stimulus pulses having energy levels in the range of those normally associated with cardiac pacing. To this end, the inventors have determined that while it is possible to capture heart tissue adjacent an electrode during fibrillation by delivery of a pacing pulse during the excitable gap, the specific timing of the pulse within the gap is important in determining the degree of excitation and the uniformity of the activation waveform produced. Pacing earlier in the excitable gap when the dispersion of refractoriness/excitability is high results in slow and non-uniform propagation of the evoked response, while pacing late in the excitable gap provides a more uniform activation waveform extending from the tissue adjacent the pacing electrode.

The inventors have determined that, to the extent that capture of a desired amount of heart tissue is desired in order to terminate fibrillation, precise timing of delivered pacing pulses relative to the excitable gaps at the pacing sites is beneficial. To this end, in one aspect of the invention a monophasic action potential (MAP) type electrode is employed as the sensing electrode, allowing for precise measurement of the depolarization waveform and enhancing the ability to provide precisely timed pacing pulses relative to the local excitable gap.

In order to terminate fibrillation, it is necessary not only to reliably capture tissue at a multiplicity of sites, it is also necessary that the sites be synchronized so that ultimately a desired amount of heart tissue can be simultaneously depolarized, allowing the heart to begin beating in a synchronized fashion thereafter. To this end, another aspect of the invention provides a mechanism for gradually converging the polarization/depolarization cycles of the multiple pacing sites. Preferably, the invention is embodied in a device which, upon achieving a desired degree of synchronization at the multiple pacing sites, ceases delivery of pacing pulses for a period of time to allow the heart to resume beating in a synchronized fashion on its own. In the event that the heart does not resume beating in a synchronized fashion, the multiple site pacing therapy may be delivered anew.

In a preferred embodiment of the invention, pacing pulses are delivered at multiple sites on or in the fibrillating chamber or chambers of the heart, each pulse timed to fall within an acceptable portion of the excitable gap of the tissue adjacent the pacing electrode. Based upon the polarization/depolarization cycle at each of the pacing sites, the device determines a sequence of optimal times for delivery of pacing pulses at each site, so that the pacing pulses will occur in that portion of the excitable gap most likely to produce uniform activation wavefronts. The actual delivery times of the pacing pulses are varied from the calculated optimal pulse delivery times in order to converge the depolarization/repolarization cycles at the various sites, constrained by the requirement of delivery of pacing pulses within the desired portion of the excitable gap. Because tissue sites which have longer polarization/depolarization cycles typically have longer excitable gaps, greater amounts of variability in the actual times of delivery of a pacing pulses at such sites are possible.

Preferably, after delivery of a pacing pulse or sensing of an intrinsic depolarization, the optimal times for delivery of pacing pulses thereafter at the pacing sites are recalculated, along with actual pulse delivery times selected to synchronize the pacing sites. At such time as pacing pulses are delivered at all paced sites or at a predetermined proportion of paced sites result in a desired amount of the heart tissue being simultaneously depolarized, the device may cease delivery of pacing pulses and monitor the intrinsic polarization/depolarization cycles at the various pacing sites in order to determine whether the fibrillating heart chamber or chambers have been successfully synchronized.

BRIEF DESCRIPTION OF THE DRAWINGS

FIGS. 1, 2, 3, 4, 5, 6 and 7 are plan views of alternative embodiments of pacing/sensing leads adapted for use in conjunction with the present invention.

DETAILED DESCRIPTION OF THE PREFERRED EMBODIMENT

Figure 1:
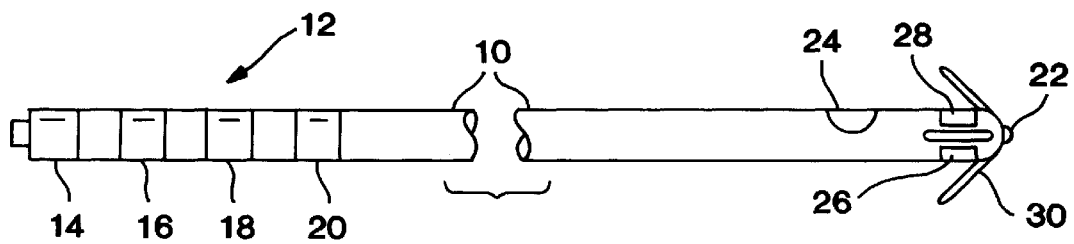

FIGS. 1–7 are illustrations of various leads which may be employed in conjunction with the present invention. Each of the illustrated leads includes a small surface sensing electrode intended for positioning adjacent the cardiac tissue and typically 5 millimeters square or smaller, and a second sensing electrode located spaced therefrom. These two sensing electrodes make up the monophasic action potential (MAP) type electrode that are employed to sense atrial depolarization waveforms in conjunction with the present invention. In conjunction with each monophasic action potential sensing electrode pair a pair of pacing electrodes is provided, allowing for pacing closely adjacent to the sensing electrode which is in contact with the cardiac tissue. Within this general organizational constraint, a variety of leads may be produced, as illustrated in FIGS. 1–7. The lead of FIG. 1 comprises an elongated insulative lead body carrying an inline multipolar connector assembly 12 at its proximal end. Connector assembly 12 includes four connector rings, 14, 16, 18 and 20 and may correspond to that illustrated in U.S. patent application Ser. No. 08/846,008, filed Apr. 25, 1997 now U.S. Pat. No. 5,843,141 by Ries et al, incorporated herein by reference in its entirety. Other conventional connector assemblies may of course be substituted. At its proximal end, the lead carries a small hemispherical electrode 32 intended to contact heart tissue for sensing atrial depolarization waveforms and a second sensing electrode 24 located approximately 5 millimeters proximal to the tip electrode 22 and recessed with respect to the outer surface of the lead body 10. Electrodes 22 and 24 make up the MAP type electrode pair employed for sensing atrial depolarizations. Pacing electrodes 28 and 30 are closely adjacent the tip of the lead, allowing for delivery of pacing pulses to tissue in the vicinity of electrode 22. Tines 30 are provided in order to stabilize the lead at a desired location. While illustrated as generally straight in configuration, lead body 10 may be provided with a preformed curved configuration, for example a J-shaped configuration if electrode 22 is to be located in the right atrial appendage. Lead body carries four conductors (not illustrated) which couple connector rings 14, 16, 18 and 20 to electrodes 22, 24, 26 and 28.

Figure 2:
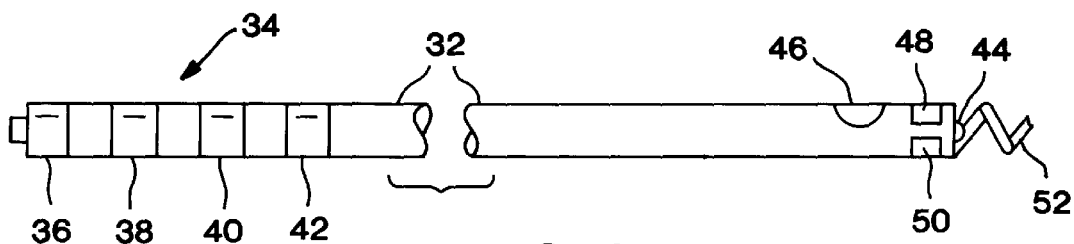

FIG. 2 is a plan view of an alternative embodiment of a lead for use in conjunction with the present invention. Like the lead of FIG. 1, it comprises an elongated insulative lead body 32 carrying connector rings 36, 38, 40 and 42. At its proximal end, the lead is provided with a small surface tip electrode 44 and a recessed sensing electrode 46, corresponding to electrodes 22 and 24 in FIG. 1. These two electrodes make up the MAP type electrode pair employed for sensing atrial depolarizations. Pacing electrodes 48 and 50 correspond to electrodes 26 and 28 in FIG. 1 and are employed to pace the heart tissue adjacent the electrode 44. A fixation helix 52, not coupled to any of the electrodes in the illustrated embodiment is provided to allow for stabilization of electrode 44 adjacent heart tissue. Helix 52 is preferably fabricated of a rigid, non-conductive material, or if fabricated metal is preferably covered with an insulated coating. Lead body 32 carries four conductors (not illustrated) which couple connector rings 36, 38, 40 and 42 to electrodes 44, 46, 48 and 50.

Figure 3:
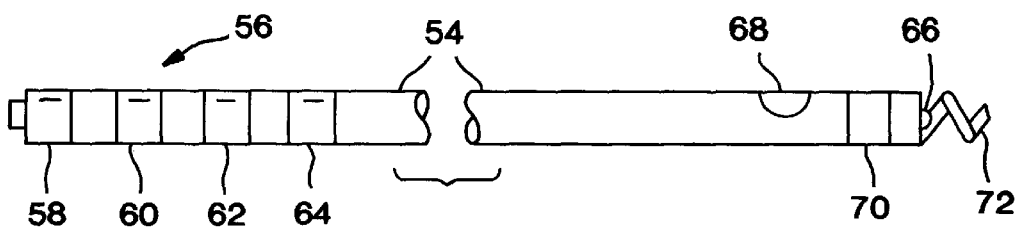

FIG. 3 is an additional alternative embodiment of a transvenous lead for use in conjunction with the present invention. Like the leads of FIG. 1 and FIG. 2 it has an elongated insulative lead body 54 which carries at its proximal end an in-line connector assembly 56 including connector rings 58, 60, 62 and 64. At its proximal end, the lead carries a small surface area, hemispherical electrode 66 and a recessed electrode 68, corresponding to electrodes 22 and 24 (FIG. 1). These electrodes make up the MAP type electrodes that are employed for sensing atrial depolarizations. The lead also includes a helical electrode 72 which is adapted to be screwed into heart tissue and a ring electrode 70. Electrodes 70 and 72 are employed to pace the heart tissue in the vacinity of tip electrode 66. Lead body 54 carries four conductors (not illustrated) which couple connector rings 58, 60, 62 and 64 to electrodes 66, 68, 70 and 72.

FIG. 4 is a first embodiment of an epicardial lead adapted to be employed in conjunction with the present invention. This lead comprises an elongated insulative lead body 74 carrying an in-line connector assembly 76 comprising connector rings 78, 80, 82 and 84. At its distal end, the lead body is provided with an insulative pad 86 adapted to be sutured against heart tissue by means of suture passed through suture holes 88. A small surface area hemispherical electrode 94 is mounted on the lower surface of pad 86, and is adapted to contact heart tissue. Atrial depolarizations are sensed between electrode 94 and a second sensing electrode (not visible in this view) located on the upper surface of pad 86 or alternatively along lead body 74, proximal to pad 86. Electrode 94 and the additional sense electrode make up the MAP type electrode pair employed for sensing atrial depolarizations in conjunction with the present invention. Pacing electrodes 90 and 92 are employed to pace cardiac tissue in the vicinity of pacing electrode 94. Lead body 74 carries four conductors (not illustrated) which couple connector rings 78, 80, 82 and 84 to electrodes 90, 92,84 and the un-illustrated sensing electrode.

FIG. 5 is an alternative embodiment of an epicardial lead according to the present invention, in this case providing for pacing at multiple sites on a chamber of the heart. This lead is provided with an elongated insulative lead body 96 which carries at its proximal end a bifurcated in-line connector assembly 98 carrying connectorrings 100, 102, 104, 106, 108, 110, 112, 114, 116 and 118. At its distal end the lead is provided with an insulative pad 120 which is adapted to be secured against heart tissue by means of sutures passed through suture holes 122. The lead is provided with three small surface hemispheric electrodes 126, 134 and 140 adapted to contact heart tissue. Signals are sensed between these electrodes and an additional sense electrode, not visible in this view, located on the upper surface of pad 120 or along lead body 96, proximal to pad 120. Electrodes 128, 134 and 140 along with the additional unillustrated sense electrode make up three MAP type sensing electrode pairs. Three pacing electrode pairs including electrodes 124 and 126, electrodes 130 and 132 and electrodes 136 and 138 are employed to pace heart tissue adjacent electrodes 128, 134 and 140, respectively. Lead body 96 carries 10 conductors (not illustrated) which couple connector rings 100, 102, 104, 106, 108, 110, 112, 114, 116 and 118 to electrodes 124, 126, 128, 130, 132 134, 136, 138, 140 and the un-illustrated sensing electrode.

Figure 6:
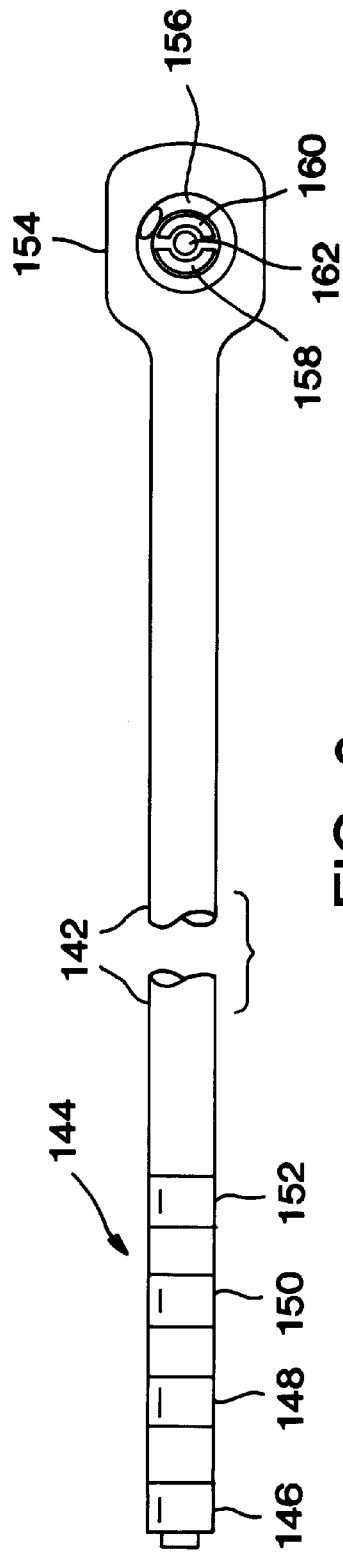

FIG. 6 is an additional alternative embodiment of an epicardial lead for use in conjunction with the present invention. Like the lead of FIG. 4, it is provided with an elongated insulative lead body 142 carrying at its proximal end an in-line connector assembly 144 comprising connector rings 146, 148, 150 and 152. At its proximal end, the lead carries an insulative pad 154 which has on its lower surface, a small surface hemispheric electrode 162 adapted to contact heart tissue. A second sensing electrode, not visible in this view, operates in conjunction with electrode 162 to provide an MAP type sensing electrode pair for sensing atrial depolarization waveforms. The remote sensing electrode may be on the upper surface of pad 154 or located proximal to pad 154 along lead body 142. In addition, the lead is provided with a fixation helix 156 which extends downward from the lower surface of pad 154 and is screwed into heart tissue, maintaining electrodes 158, 160 and 162 in contact with heart tissue. Helix 156 is preferably fabricated either of an insulative material, or a fabricated metal, provided with an insulative coating. Lead body 142 carries four conductors (not illustrated) which couple connector rings 146, 148, 150 and 152 to electrodes 158, 160, 162 and the un-illustrated sensing electrode.

Figure 7:
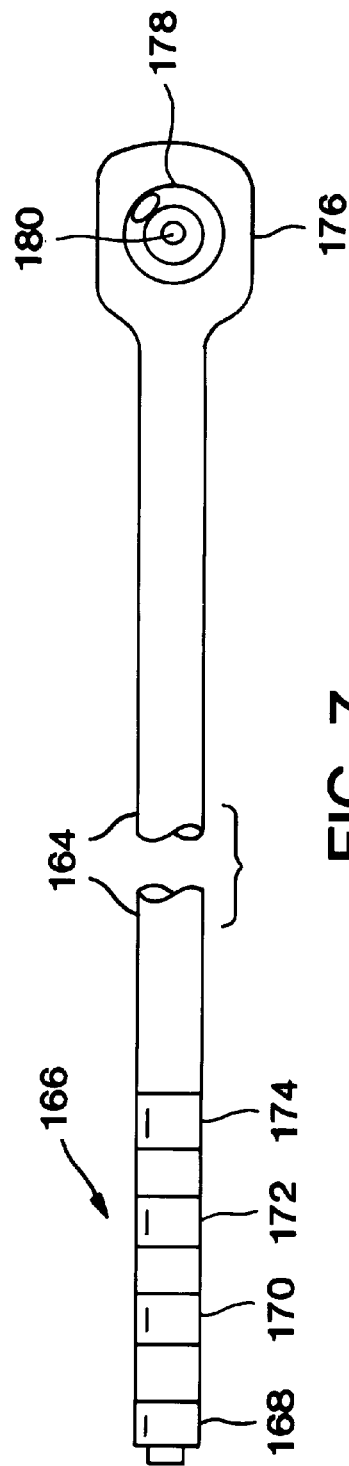

FIG. 7 is a plan view of yet an additional alternative epicardial electrode for use in conjunction with the present invention. Like the lead of FIG. 4 it is provided with an elongated insulative lead body 164 which carries at its proximal end an in-line connector assembly 166 comprising connectors 168, 170, 172 and 174. At its distal end, the lead carries an insulative pad 176 which carries on its lower surface a small surface hemispheric electrode 180 intended to contact heart tissue. A helical electrode 178 is provided extending from the lower surface of pad 176, adapted to be screwed into heart tissue. Two additional electrodes (unillustrated) are provided which may be located on the upper surface of pad 176 or along lead bodies 164 proximal to pad 176. One of the two additional electrodes serves in conjunction with electrode 180 to form an MAP type electrode pair for sensing atrial depolarizations. The other of the two additional electrodes serve in conjunction with helical electrode 178 to pace heart tissue adjacent electrode 180. Lead body 164 carries four conductors (not illustrated) which couple connector rings 168, 170, 172 and 174 to electrodes 178, 160 and the two un-illustrated sensing and pacing electrodes.

Figure 8:
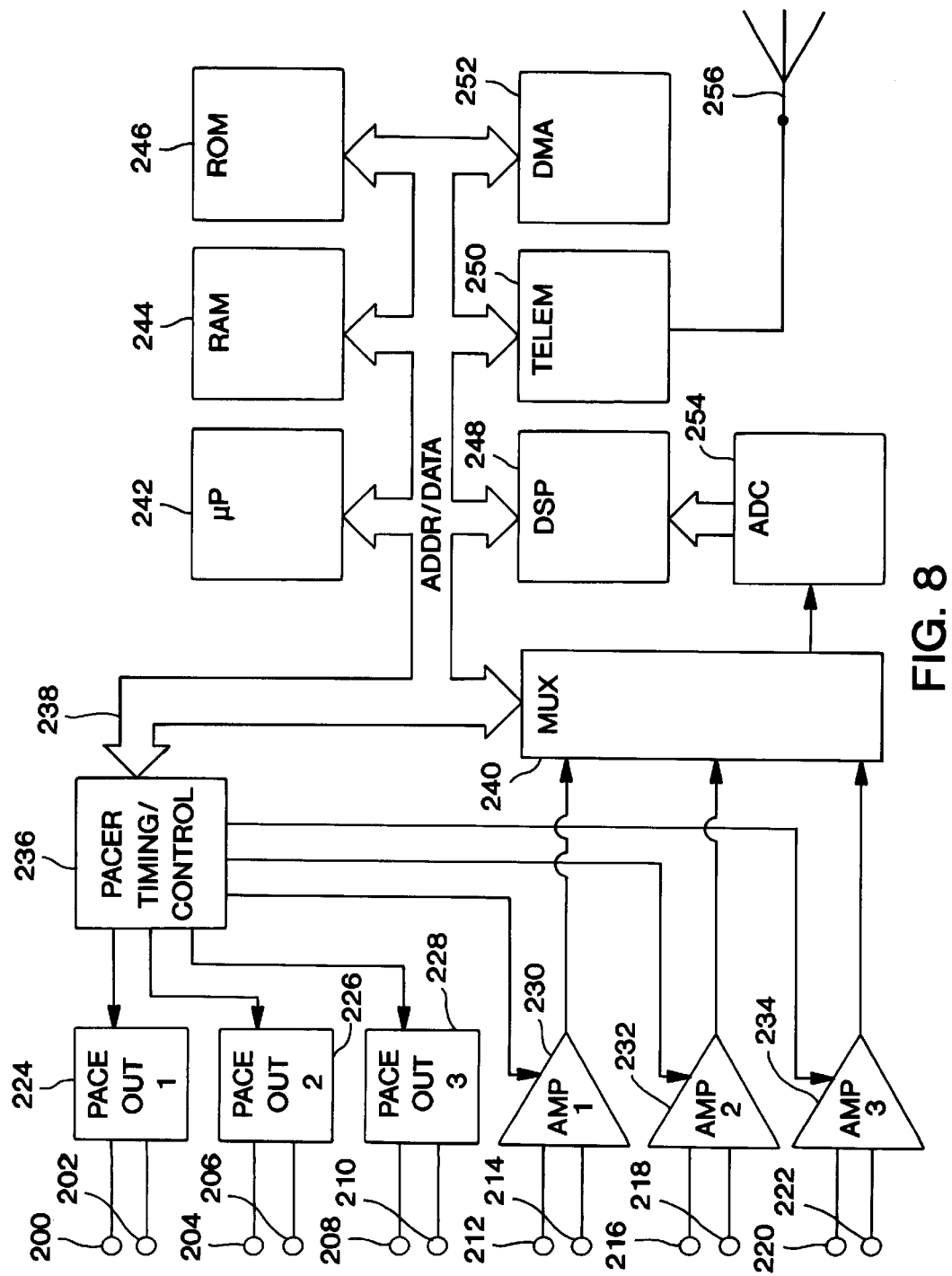
FIG. 8 is a functional schematic diagram of a pacemaker embodying the present invention.

FIG. 8 is a block diagram illustrating the major functional components of an implantable pacemaker embodying the invention, in this case directed toward termination of atrial fibrillation. Timing and control functions are preferably accomplished using a microprocessor based system, corresponding to those used in presently available pacemakers. The basic function and operation of the timing and control logic 236, microprocessor 242, random access memory 246 and read only memory 244 may correspond to corresponding elements in the microprocessor controlled systems disclosed in U.S. Pat. No. 4,407,288 issued to Langer et al. on Oct. 4, 1983, U.S. Pat. No. 5,022,395, issued to Russie on Jun. 11, 1991, U.S. Pat. No. 4,958,632 issued to Duggan on Sep. 25, 1990 or in U.S. Pat. No. 4,830,006 issued to Haluska et al. on May 16, 1989, all of which are incorporated herein by reference in their entireties.

Pacing pulses are delivered by pacemaker output circuits 224, 226 and 228, via electrodes 200, 202, 204, 206, 208 and 210, triggered by pacer timing/control circuitry 236. Timing of delivery of pacing pulses is calculated by microprocessor 242 according to the methodology of the present invention and communicated to timing/control circuitry 236 via address/data bus 238. The pacing output circuits 224, 226 and 228 may correspond generally to the output circuitry illustrated in U.S. Pat. No. 4,406,286 issued to Stein on Sep. 27, 1983 or U.S. Pat. No. 4,340,062 issued to Thompson et al. on Jul. 20, 1982, both of which are also incorporated herein by reference in their entireties, Timing/control circuitry 236, in conjunction with microprocessor 242 also detects the occurrence of atrial fibrillation based on atrial depolarizations sensed via one or more of electrodes 212, 214, 216, 218, 220 and 222, via one or more of sense amplifiers 230, 232 and 234. The outputs of amplifiers 230, 232 and 234 are provided to multiplexer 240, digitized by A/D converter circuit 254 and processed by digital signal processing circuit 248 to determine the start points and end points of the atrial depolarizations at the various pacing sites. This information is provided to the microprocessor 242 via address/data bus 238 and is employed by the microprocessor both to detect atrial fibrillation and to determine the times for pacing pulse delivery at the various pacing sites. Atrial sensing amplifiers 230, 232 and 234 can be any conventional cardiac sense amplifier circuits equivalent to any prior art atrial cardiac sensing circuits employed in previous devices. For example, the sense amplifiers may correspond to the circuits disclosed in U.S. Pat. No. 4,266,551 issued to Stein on May 21, 1981, U.S. Pat. No. 4,275,737 issued to Thompson et al, U.S. Pat. No. 4,649,931 issued to Beck on Mar. 17, 1987, all of which are incorporated herein by reference in their entireties. Digital signal processing circuit 248 may correspond to any of a number of currently available digital signal processing circuits, such as those manufactured by Analog Devices and Texas Instruments, for example one of the TMS320 series of digital signal processors, configurable to perform digital filtering, edge detection and other signal processing functions.

Detection of atrial fibrillation may be accomplished by microprocessor 242 using any of the various detection methodologies known to the art. Generally, atrial fibrillation may be detected in response to an extended series of high rate (e.g. greater than 240 b.p.m.) atrial depolarizations. If greater specificity for atrial fibrillation is desired, analysis of regularity of rate and/or waveform morphology may also be employed. Termination of atrial fibrillation may be detected in response to a decrease in the rate of atrial depolarizations and/or an increase in their regularity. In the illustrated embodiment, electrodes 212–222 correspond to the pairs of MAP electrodes illustrated in FIGS. 1–7. Exemplary detection methodologies based on atrial sensing are disclosed in U.S. Pat. No. 5,549,641, issued to Ayers et al. and in U.S. Pat. No. 5,464,432, issued to Ifinger et al., both incorporated herein by reference in their entireties. In alternative embodiments one or more pairs of additional, non-MAP type electrodes and associated sense amplifiers may be employed for fibrillation detection.

In additional alternative embodiments of the invention, electrodes located on or in the ventricles in conjunction with one or more ventricular sense amplifiers and optionally additional non-MAP type atrial electrodes may be employed in conjunction with microprocessor 242, to detect atrial fibrillation. Exemplary detection methodologies based on atrial and ventricular sensing are disclosed in U.S. Pat. No. 5,755,736, issued to Gillberg et al., in U.S. Pat. No. 5,720, 795, issued to Greenhut et al. and in U.S. Pat. No. 5,379,776, issued to Murphy et al. and in the article "Automatic Tachycardia Recognition", by Arzbaecher et al, published in Pace, Vol. 7, May-June 1984, part II, pages 541–547 all incorporated herein by reference in their entireties.

The operation of microprocessor 242 is controlled by programming stored in read only memory 244 and in random access memory 246. The operation of the device may be altered by the physician by altering the programming stored in memory 246, using an external programmer to send the required programming information to antenna 256 and telemetry circuit 250, as is conventional in implantable stimulators. Memory 246 may also be employed for storing measured parameters, such as P-P intervals, intervals between delivered pacing pulses and the onsets of atrial depolarization, the widths of atrial depolarizations and all other measured parameters employed in fibrillation detection and in controlling delivery of pacing pulses for fibrillation termination. In alternative embodiments also employing ventricular electrodes, memory 246 may also be employed for storing other measured parameters, such P-P intervals, P-R intervals and R-wave widths and amplitudes. Memory 246 may also be employed to store digitized electrocardiograms sensed using the various electrodes provided. Communication to and from the microprocessor 242, memories 246 and 244 and control logic 236 is accomplished using address/data bus 238.

Figure 9:
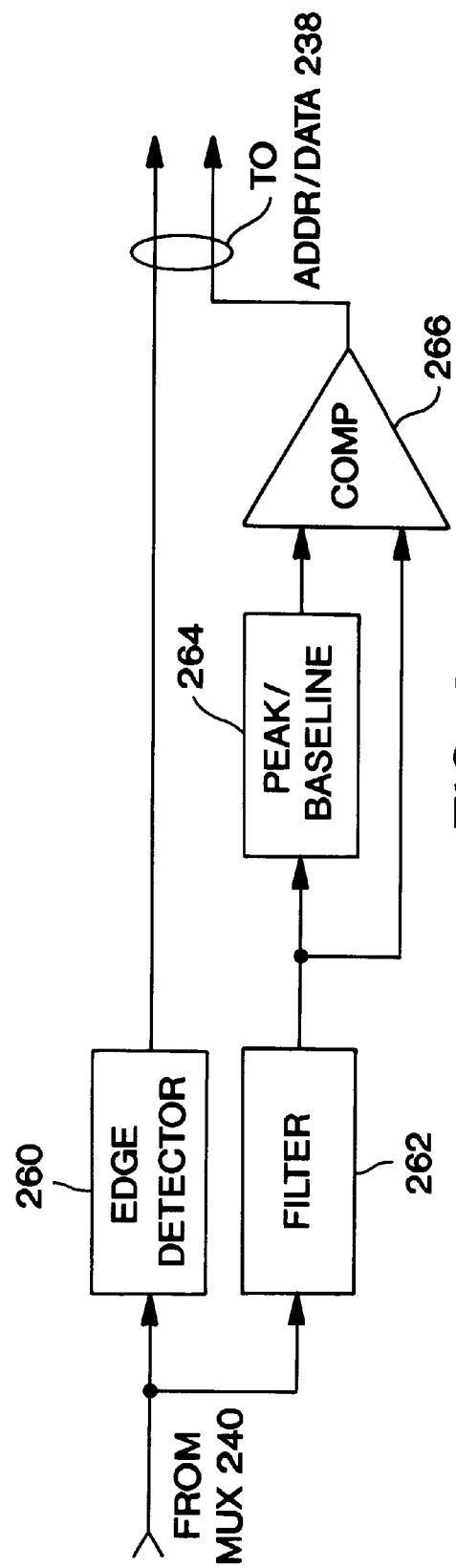
FIG. 9 is a functional schematic diagram illustrating the operation of the digital signal processor included in FIG. 8.

In conjunction with the present invention, the digital signal processing circuit 248 is configured to allow for detection of the start points and end points of atrial depolarization waveforms so that the times of their occurrence can be employed off microprocessor 242 to determine appropriate times for delivery of pacing pulses. The functional organization of the digital processing circuit is illustrated in FIG. 9. The digital signal processing circuit is configured to include an edge detector 260 which may take the form of a differentiator and a threshold detector which together detect the rapid upslope indicative of the initiation of an atrial depolarization waveform. The occurrence of the initiation of the atrial depolarization waveform is communicated to the microprocessor 242 via data/address bus 238. In addition, digital signal processing circuit 248 is configured to define a low pass filter 262, the output of which is passed through a peak/baseline circuit 264 which operates to define a sensing threshold against which the output of filter 262 is compared by comparator 266. The peak/base line circuit 264, discussed in more detail below, defines a threshold that is equal to a proportion of the peak amplitude of the present or preceding atrial depolarization waveforms against which the output of filter 262 is compared. When the output of filter 262 drops below this defined threshold, comparator 266 emits a signal to the microprocessor 242 via data/ address bus 238, indicating the end of the atrial depolarization waveform. By means of these signals, the microprocessor can determine the duration of the atrial depolarization waveform. In particular, the peak/baseline circuit operates by storing peak amplitudes and base line amplitudes of preceding waveforms, with the circuit holding the highest amplitude achieved as the peak and the lowest amplitude achieved as the baseline value. The stored peak amplitude is subject to an exponential decay, for example selected such that the defined peak amplitude will decay by 40 decibels over a 60 second time period. To the extent that amplitudes exceed the stored peak amplitude, they replace the stored peak amplitude. Likewise, to the extent that baseline values are less than the stored baseline, they replace the stored baseline value. The circuit defines a percentage (R %) of the difference between the stored base line and stored peak amplitudes, for example 10% to 40% of the difference between the stored peak and base line, and outputs this signal to comparator 266. As noted above, the signal from filter 262 falling below the defined threshold R % results in a signal from comparator 266 indicating the defined end point of the atrial depolarization waveform.

Figure 10:
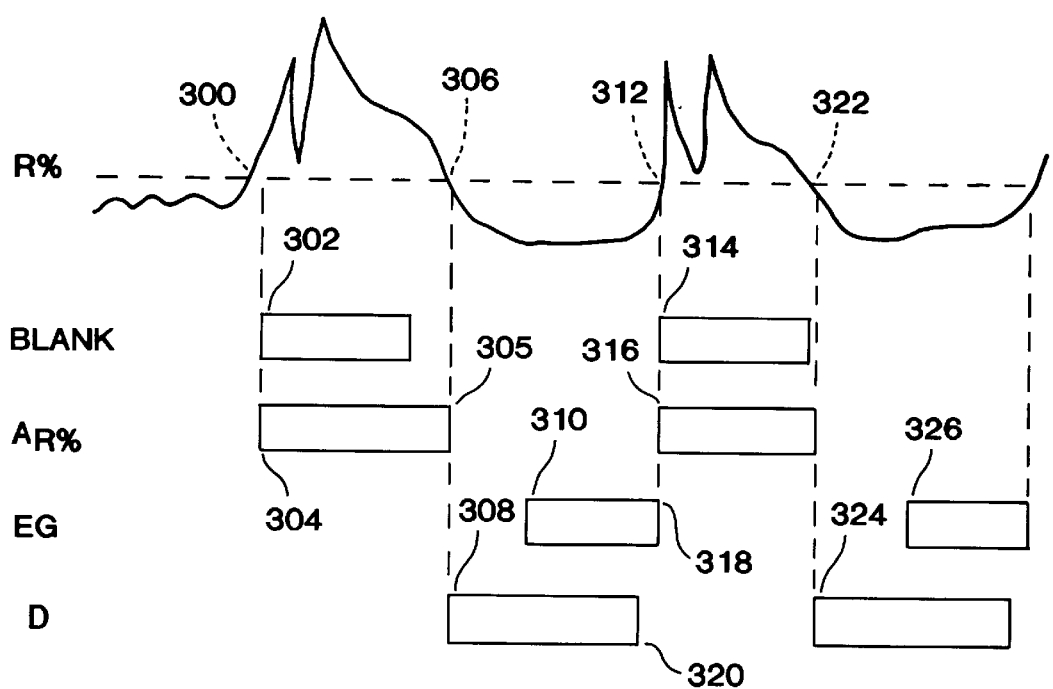
FIG. 10 is a simulated atrial electrogram and associated timing diagram illustrating measurement of atrial depolarization waveform width according to the present invention.

FIG. 10 illustrates the operation of the digital signal processing circuit, in conjunction with detection of the start points and end points of atrial depolarization waveforms. At 300, the edge detector 260 (FIG. 9) is triggered, indicating the start point of the atrial depolarization waveform. This signal is provided to the microprocessor 242 (FIG. 8) which in turn causes pacer timing/control circuitry 236 (FIG. 8) to define a digital blanking period, during which the microprocessor will not recognize subsequent edges detected by the edge detector as start points for atrial depolarization waveforms. This feature is desirable in that, as illustrated, a single atrial depolarization waveform may have the potential for triggering the edge detector more than once. At 306, the amplitude of the depolarization waveform falls below the defined threshold R %, which as discussed above is the percentage of the difference between preceding peak and base line values for the wave form or previous waveforms. This in turn allows the microprocessor to determine the duration or width ($A_R$ %) of the waveform extending from 304, at the initiation of the waveform to 305 at the point the waveform falls below the R % threshold.

Preferably, the delivered stimulus should be delivered late in the excitable gap (EG) following the depolarization waveform, a time period not determined by the pacemaker but illustrated in the timing chart as extending from 310, beginning somewhat after the end point of the atrial depolarization waveform and extending until 318, the beginning of the next atrial depolarization waveform. In operation, the pacemaker defines a delay D initiated at 308 concurrent with detection of the end point of the atrial depolarization waveform and extending until a point 320, calculated to occur late in the excitable gap 310. If the pacing algorithm were active, a pacing pulse would be delivered at the end of delay D at 320. At 312, a subsequent edge is detected, initiating a new blanking period at 314 and a new measured atrial depolarization waveform measurement at 316. At 322, the value drops below the defined threshold R %, initiating calculation of a new delay D, adapted to position the delivery of a stimulation pulse late in the excitable gap 326 as illustrated.

The duration of delay D, following the end of depolarization waveform is updated with each measured depolarization waveform, in an effort to determine the optimum time of delivery relative to the associated excitable gap period. In particular, the duration of the delay D is calculated according to the following equation:

$$D = D_{min} + \lambda A_R \% + \beta P$$

wherein $D_{min}$ is the minimum delay (e.g., 0–500 milliseconds), $\lambda$ is a dimentionless constant (e.g. 0–10), and $\beta$ is an increase in the delay for each consecutive paced interval (e.g. 0–100 milliseconds per paced interval). By this mechanism, the duration of the delay D is increased with increases in the width $A_R$ % of the atrial depolarization waveform and in response to a greater number of successive delivered pacing pulses, indicating that the pacing pulses have been successful in capturing local heart tissue. The value of the constant $\lambda$ will vary as a function of the percentage of the difference between the peak and base line values employed as the threshold R % For example, if it is easier and more accurate to detect the end of the depolarization waveform when it falls to less than 50% of the difference between the peak and stored base line values, a larger value for $\lambda$ would be employed than if the end point of the depolarization waveform was detected in response to the amplitude falling to less than 10% of the difference between the stored peak and base line values.

Figure 11:
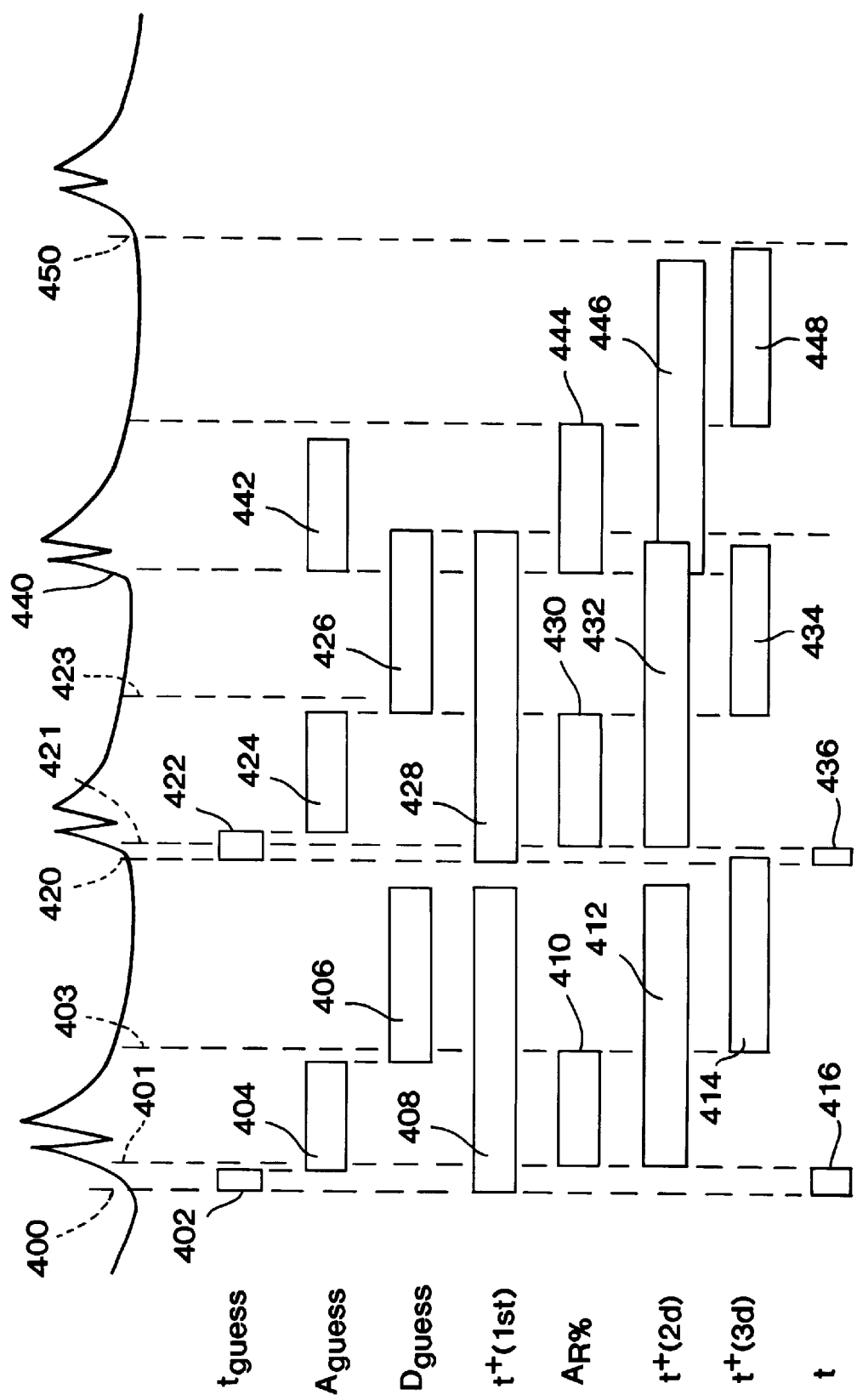
FIG. 11 is a simulated atrial electrogram illustrating measurement and control functions associated with delivery of pacing pulses according to the present invention.
Figure 12:
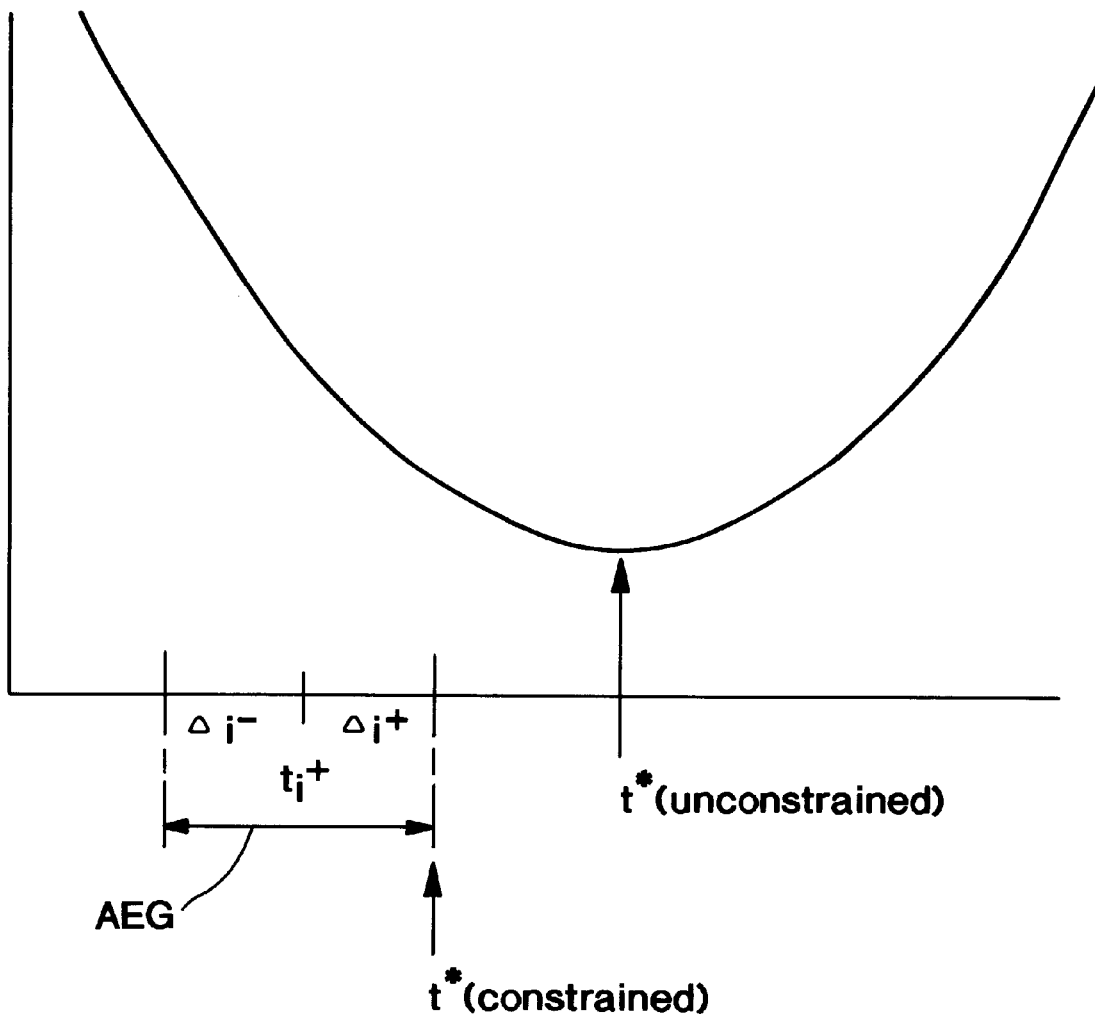
FIG. 12 is a diagram illustrating the method of calculation of the time for next delivery of a pacing pulse at a single site, according to the present invention.
Figure 13:
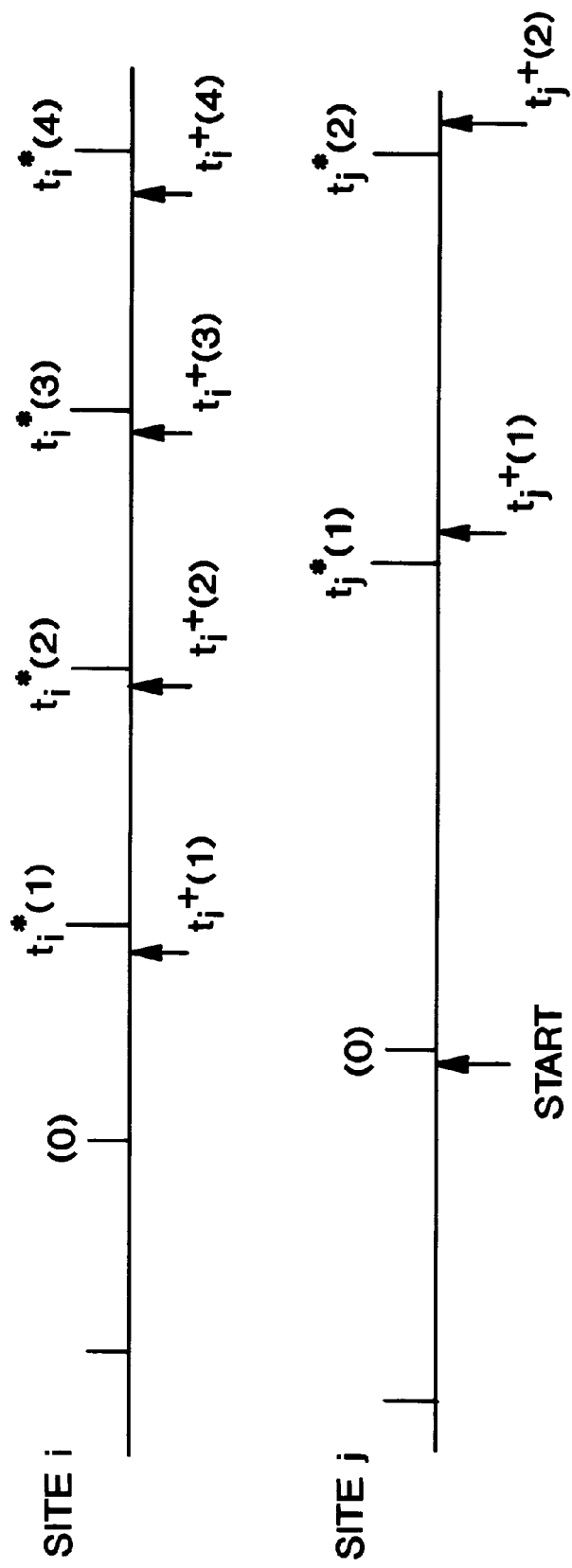
FIG. 13 is a timing diagram illustrating calculation of delivery times for multiple pacing pulses at differing sites, according to the present invention.

While the equation described in conjunction with FIG. 10 allows for accurate calculation of an optimal time to pace at a single site, following a preceding atrial depolarization, calculating optimal times to pace at multiple sites, in order to converge the polarization/depolarization cycles at multiple sites is substantially more complex. In order to accomplish this desired result, it is necessary that optimum times to pace each of the sites be calculated not only based on the preceding atrial depolarization waveform at the site, but also based on the occurrences of the atrial depolarization waveforms at the other sites. This is because it is necessary to perturb the delivered pacing pulses from the optimum delivery times for individual sites in order to cause the tissue adjacent the various pacing sites to become resynchronized. Because pacing at the various sites is not generally synchronized, the inventors have determined that it is beneficial to update the time of next delivery of a pacing pulse at a particular site each time an event occurs at that site or at any of the other sites which would affect a calculation of the next optimal times to pace. For this reason, in a preferred embodiment of the invention, calculation of optimal times to pace at each site are updated in response to each occurrence of a start point or an end point of an atrial depolarization at any of the various sites and in response to delivery of a pacing pulse to any of the sites. At each site, an optimum time to the next delivered pacing pulse is therefore calculated following a pacing pulse, recalculated on initiation of an atrial depolarization waveform thereafter, and again recalculated on detection of the end of the atrial depolarization. Updated values of the optimum times to pace are employed by the device in calculating the actual times to pace the various sites, with the actual times to pace being updated in response to each updating of the determined optimal pacing times for each site. FIG. 11 illustrates the process for updating the optimal times to pace at a single site, while FIGS. 12 and 13 illustrate the use of the updated optimal pacing times at each site to calculate actual pacing times for all sites.

FIG. 11 illustrates calculation of optimal times to pace at a single site, according to the present invention. The optimal time to pace is expressed as the term "$t^+$", which is the increment of time remaining until the optimal time to pace, as measured from the calculation point for the optimal time to pace. Initially, on delivery of a pacing pulse at 400, the first calculation of $t^+$, hereafter referred to as $t^+$ (first) is calculated according to the following equation:

$$t^+ = \tau_{guess} + A_{guess} + D_{guess} = \tau_{guess} + A_{guess} + D_{min} + \lambda A_{guess} + \beta P$$

The value $\tau_{guess}$ at 402 is the device's best estimate as to the time between the pacing pulse and the time at which the atrial depolarization waveform initiation point will be detected. This may be, for example, the measured time between these two events associated with the preceding atrial paced depolarization. $A_{guess}$ is the device's best estimate as to the likely duration of the atrial depolarization and may correspondingly be the measured duration of the preceding atrial depolarization. $D_{guess}$ is an estimate of the delay D from the end of the estimated atrial depolarization $A_{guess}$ to the optimum delivery time for pacing pulse period, calculated based on $A_{guess}$. Following delivery of the pacing pulse at 400, the values of $t_{guess}$ 402, $A_{guess}$ 404, $D_{guess}$ 406 and the first value of $t^+$ are calculated. The value of $t^+$ so calculated is correspondingly used after delivery of pacing pulse 400 to update the calculations of the actual times for delivery of pacing pulses at the various sites.

On detection of the start point of the atrial depolarization at 401, signaling the beginning of the measured duration $A_R$ % of the depolarization, the value of $t^+$ is recalculated to provide a second value of $t^+$ at 412, calculated according to the following equation:

$$t^+ = A_{guess} + D_{min} + \lambda A_{guess} + \beta P$$

This calculation provides a corrected value of $t^+$, based upon the actual time of occurrence of the start point of the atrial depolarization, as opposed to the estimated time of occurrence. This new value of $t^+$ is to recalculate the actual times of pulse delivery for all paced sites. At 403, the amplitude of the depolarization waveform falls below the defined threshold R %, signifying the end of the measured atrial depolarization waveform at 410 and causing recalculation of the value of $t^+$ to provide a third value 414 for an optimal time for pacing pulse delivery at the site, using the following equation:

$$t^+ D_{min} + \lambda A_{R\,\%} + \beta P$$

This optimal time of delivery is combined with the extent optimal times for pulse delivery at the other sites in order to derive the actual times of pulse delivery at all sites.

At 420, a pacing pulse is delivered at the then calculated actual time of pulse delivery at the paced site. It should be noted that, in this case, the actual time of delivery is somewhat before the optimal time of delivery $t^+$, due to the operation of the device to attempt to synchronize the various sites as discussed in more detail below. On delivery of a pacing pulse at 420, a new value of $t^+$ 428, is calculated, comprising the sum of $\tau_{guess}$ 422, which is equal to the actual time $\tau$ between the delivered pacing pulse 400 and detection of onset of the preceding depolarization at 401, plus $A_{guess}$ 424 which is equal to the actual measured value of $A_{R\,\%}$ associated with the preceding depolarization and $D_{guess}$, calculated based upon the equations described above. Correspondingly, a second value of $t^+$ (432) is calculated on sensing of the actual start point of a depolarization waveform at 421 and a third value of $t^+$ (434) is calculated upon detection of the end point of the atrial depolarization at 423. In the case illustrated, the next atrial depolarization start point at 440 precedes the scheduled actual delivery time for a pacing pulse at the site. In this case, a new estimate of the value of the next optimal time to pace $t^+$ is calculated at 446, corresponding to the mechanism for calculating the second value of $t^+$ associated with the two preceding depolarizations and a second, updated value of the optimal time to pace $t^+$ is calculated at 448, corresponding to the method of calculating the third value of an optimal time to pace associated with the two preceding depolarizations. At 450, on expiration of a calculated actual time for delivery of the pacing pulse at the pacing site, a pacing pulse is delivered. It should be noted that in this case, delivery of the pacing pulse occurred after the second calculated optimal time for delivery $t^+$ (448), the timing being perturbed in order to attempt to synchronize the various pacing sites, as discussed in more detail below.

FIG. 12 illustrates the mechanism by which the actual time $t^*$ for delivery of a pacing pulse at a particular pacing site is calculated. In order to cause polarization/depolarization cycles at the various pacing sites to converge, the device perturbs the times of delivery of pacing pulses from the calculated optimum best times to pace ($t^+$) for each pacing site to an actual time for pacing delivery $t^*$ for each site, which optimizes the tradeoff between local capture and global synchronization. The optimization process employed by the device derives a set of actual times to pace $t^*$ which minimizes a quadratic objective function $\Phi$ of deviations from the values of $t^+$, as well as cycle length and temporal differences for activation at and the different pacing sites, according to the following equation:

$$\Phi = \sum_{i=1}^{N} w_i [t_i - t_i^+]^2 + \sum_{i=1}^{N-1} \sum_{j=i+1}^{N} [(t_i + \tau_i) - (t_j + \tau_j)]^2$$

Optimization of $\Phi$ is completed for each activation k subject to the constraints set by the following equation:

$$\max(t_i^+ - \Delta^-_i, 0) \leq t^*_i \leq t_i^+ + \Delta^+_i$$

As illustrated in FIG. 12, the value of $t^*$ unconstrained, may fall too far from the optimal time $t^+$ for pacing at the particular site. For this reason, the above equation defines a time interval AEG corresponding to an acceptable excitable gap during which the pacing pulse can be delivered. If $t^*$ falls within AEG, it is delivered as initially calculated. If $t^*$ falls outside of AEG, it is delivered at the end point of AEG nearest to the calculated unconstrained value of $t^*$, as illustrated in FIG. 12.

The optimization methodology described above is invariant with respect to the time reference selected. Since it is convenient to think of a scheduled time to pace as a positive time in the future which decrements toward zero as time marches forward, the current time will always be zero. Events which have occurred in the past will have negative times which grow more negative as time moves forward. For a pacing site I, the set of values of $t_i^*$ for that site, computed at one instant will therefore decrement towards zero as time marches forward until either a pacing pulse is delivered or it is necessary to recompute the values of $t_i^*$. Recomputation of $t_i^*$ is required whenever a pacing pulse at any site is rescheduled (i.e., whenever the value of the optimum time to pace $t_i^+$ for that site is recalculated.

The first summation term in $\Phi$ ($w_i [t_i - t_i^+]^2$) measures deviations from the best time to capture locally at each site, i.e., the weighting coefficients $w_i$ along with the constraints on $t_i^*$ reflect how important that the pacing pulse occur exactly at $t_i^+$. Larger values of $w_i$ increase the impact of deviations from $t_i^+$ on the objective function relative to the other terms. Ideally, the weighting coefficients $w_i$ could be constant giving a simpler and more robust control algorithm. If the excitable gap increases as control is maintained, however, the weighting coefficients may be a function of time at each site which depends upon the degree of local control. When a local site is reset and is attempting to achieve recapture with a small excitable gap, the value of $w_i(k)$ may be set larger, up to a maximum ($w_{max}$). After local capture has been achieved, the value of $w_i(k)$ may be reduced to a minimum value of $w_{min}$, as the local consecutive pace count ($P_i$) increases as a constant rate ($\beta_w$), according to the following equation:

$$w_i = \max(w_{min}, w_{max} - \beta_w P_i)$$

The second summation term in $\Phi$ measures differences in phase for the activation at every pair of sites I and J. When this term is zero, activation will be simultaneous at all sites. Activation at a site I is defined as the time to pace ($t_i^+$) plus the delay to activation (beta$_i$) at site.

The constraints upon $t_i^*$ are like the weighing coefficients $w_i$ in that they keep $t_i^*$ close to the best local time to pace $t_i^{*+}$. A strategy similar to that used with the weighting coefficients may be employed to modulate the constraint rein defined by $\Delta_i^+$ and $\Delta_i^-$, as illustrated in FIG. 12 to define the acceptable excitable gap (AEG). When a site is not captured, $\Delta_i^+$ and $\Delta_i^-$ would be small, as the local consecutive pace counts the constraints may be eased by increasing $\Delta_i^+$ and $\Delta_i^-$.

The set of $t_i^+$ equals $t_i^*$ which maximizes the objective function $\Phi$ ($[(t_i + \tau_i) - (t_j + \tau_j)]^2$) is the solution to the following linear set of equations:

$$\begin{pmatrix} N-1+w_1 & -1 & \cdots & -1 \\ -1 & N-1+w_2 & & \\ \cdots & & \cdots & \\ -1 & & & N-1+w_N \end{pmatrix} \times \begin{pmatrix} t_1^* \\ t_2^* \\ \cdots \\ t_N^* \end{pmatrix} = \begin{pmatrix} w_1 t_1^+ - \delta_1 \\ w_2 t_2^+ - \delta_2 \\ \cdots \\ w_N t_N^+ - \delta_N \end{pmatrix}$$

This equation can be rewritten in compact matrix notation as:

$$At^* = wt^+ - \delta$$

The solution is:

$$t^* = A^{-1}(wt^+ - \delta)$$

Coordination of pacing and multiple sites may be accomplished by applying the linear transformation on the vectored $(wt^+ - \delta)$ o obtain the optimal time to pace vector $(t^*)$ every time there is an update to $wt^+ - \delta$. It is for this reason that an estimate of $t_i^+$ and of $\tau_i$ must be available at all times for each electrode site. Note that it is not necessary to recompute $A^{-1}$ if the weighting coefficients (w) remain constant. Further simplifications can be made if the activation delays ($\tau$) which define $\delta$ are constant or can be assumed to be zero.

The algorithm as described above assumes optimization of the time to pace will be for the next activation at all sites. Because sites may be activated out of phase and at different cycle lengths, however, activation at one site may be in the future while the associated activation at another site has already occurred in the past. Disparate cycle lengths can also cause the associated activation at the other site to be several cycles beyond the next scheduled activation. This problem is illustrated in FIG. 13 with regard to pacing pulses delivered at two sites i and j. In this diagram, shorter vertical lines extending upward from the base lines indicate sensed events, while longer vertical lines extending upward from the base line indicate paced events for each site. The events are numbered in parentheses for each pacing site in order of their occurrence. The sensed event (zero) at site J is the point at which multisite control is initiated. For the next cycle (1) the best times to pace are based on single site control $Rt_i^+(1)$ and $t_j^+(1)$ at sites i and j respectively. The multisite optimization yields $t_i^*(1)$ and $t_j^*(1)$, which delays the scheduled pace at site i and expedites the pacing pulse at site j to move activation (1) at the two sites closer together. Site i pacing occurs at $t_i^*(1)$ and a new cycle (2) starts with the single site best time to pace at $t_i^+(2)$ pacing for cycle (1) at site j has yet to occur, however, it is no longer possible to shift activation (1) at site i. Any updates to $t_j^+(1)$ after $t_i^*(1)$ require $t_j^+(1)$ to be recomputed using a constant $t_i^*(1)$ instead of $t_i^+(1)$ in order to determine $t_i^*(2)$ the multi-site optimization requires $t_j^+(2)$ to be known before activation (1) has occurred at site j. An optimistic guess for $t_j^+(2)$ is:

$$t^+_j(2) = t^*_j(1) = [t^*_j(1)$$
$$- t^*_j(0) + \beta] 2t^*_j(1) - t^*_j(0) + \beta$$

Where $t_j^*(0)$ is the time of activation (0) at site J. This guess assumes site J has activated at $t_j^*(1)$ and that $t_j^+(2)$ will be the previous cycle length plus $\beta$. Having a guess of $t_j^+(2)$ allows $t_i^*(2)$ to be computed and causes activation (2) at site I to be delayed in order to bring it closer to activation (2) at site j. After pacing site i at $t_i^*(2)$ a guess of $t_j^+(3)$ is needed to compute $t_i^*(3)$. To guess at $t_j(3)$ it is now necessary to look two cycles in advance at site j because pacing for cycle (1) has still yet to occur. When pacing at site j finally does occur at $t_j^*(1)$, the next time to pace $t_j^*(2)$ is computed using the constant $t_i^*(2)$ instead of $t_i^+(2)$ because pacing at site i for cycle (2) has already occurred at $t_i^*(2)$ and cannot be shifted. The computed $t_j^*(2)$ once again expedites the pacing pulse at site j where the activation cycle length is longer. Pacing pulses at site i where the activation cycle length is shorter, are delayed. This acts to converge not only the cycle lengths at sites i and j but also the phase difference between the sites. If pacing capture at every site is maintained, the control algorithm will eventually begin to activate sites i and j simultaneously.

Figure 14:
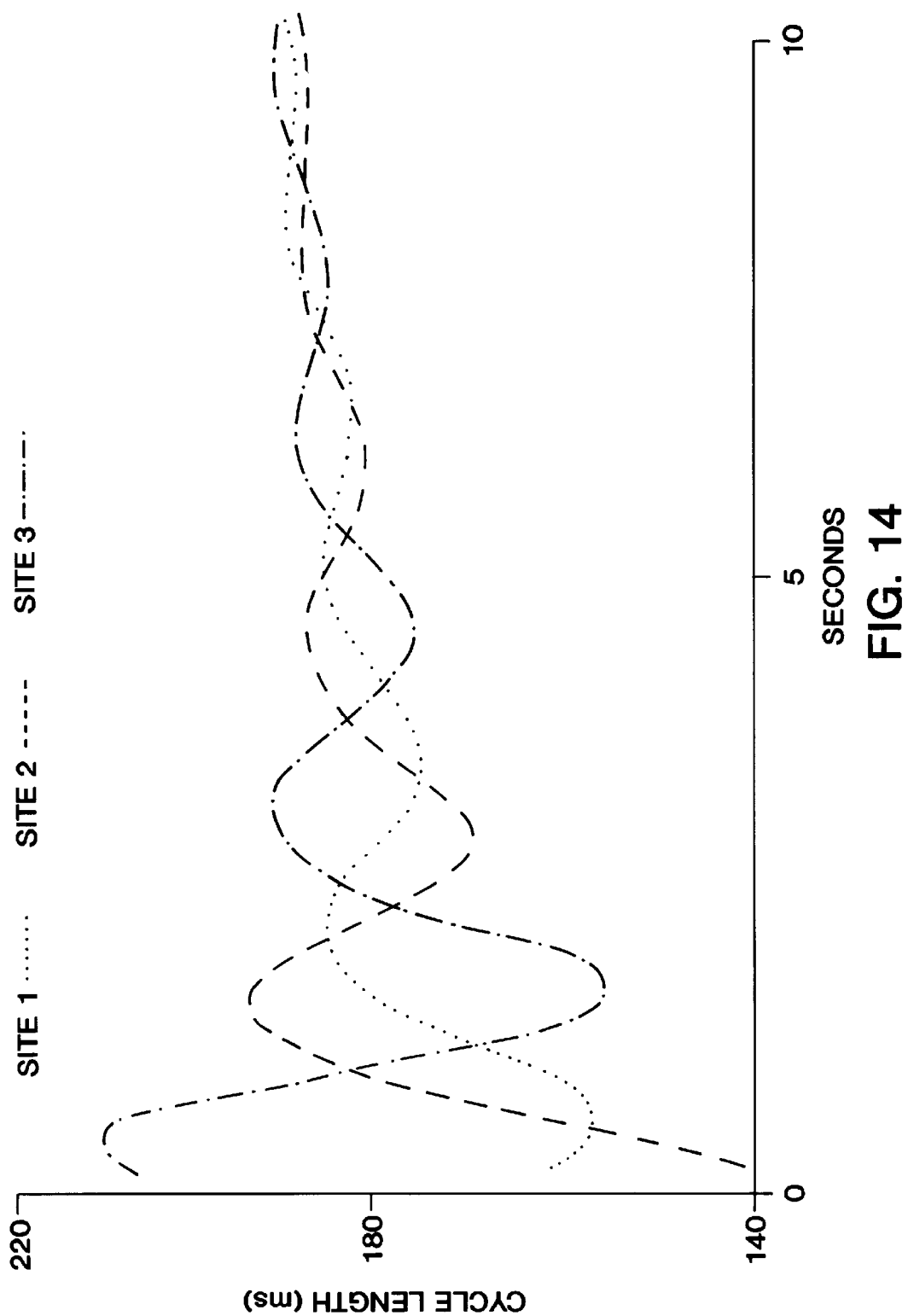
FIG. 14 is a chart illustrating variations in cycle lengths of pacing pulses delivered at three different pacing sites, resulting in resynchronization of the polarization/depolarization cycle at the three sites, according to the present invention.
Figure 15:
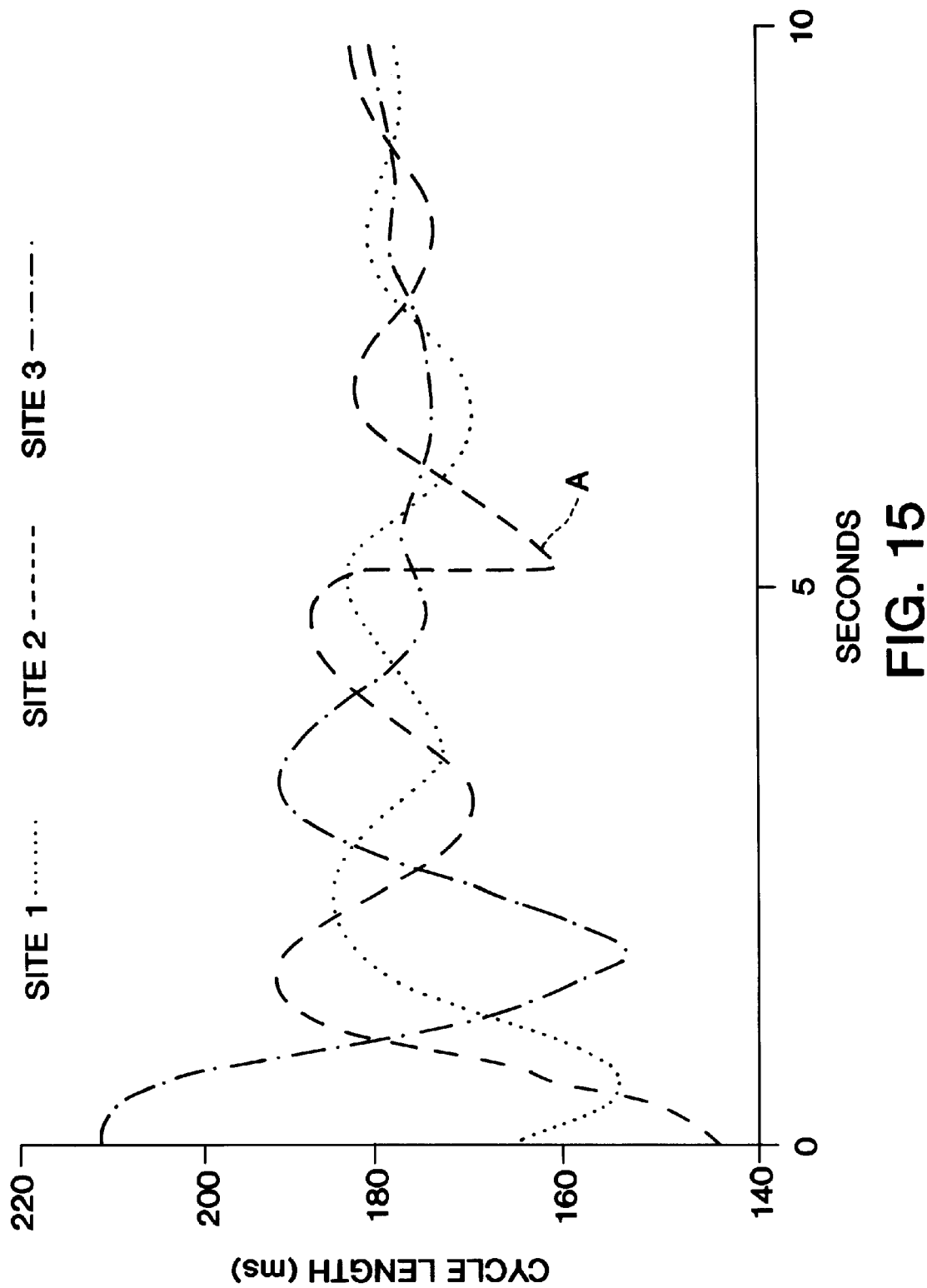
FIG. 15 is a chart illustrating variations in cycle lengths of pacing pulses delivered at three different pacing sites, illustrating resynchronization of the polarization/depolarization cycle at the three sites, even following loss of capture at one site.

The example in FIG. 13 is for two sites, however, an arbitrary number of sites can be synchronized using this technique. This is illustrated by the graphs in FIGS. 14 and show coordination of pacing at three sites according to the present invention. The weighting coefficients are all fixed at W=20, the constraint range $\Delta_i^+$ and $\Delta_i^-$ is plus or minus ten milliseconds and $\beta$ is 0.25 milliseconds per pace. As illustrated, differences in the cycle length and, although not illustrated, differences in the phase converge toward zero after about 10 seconds of multisite control. The rate of convergence of cycle length and phase will depend upon the choices of the weighting coefficients and the restraint range. Convergence will be faster with smaller weighting coefficients at a wider constraint range, but the possibility of losing capture at one of the paced sites would be greater. Larger weighting coefficients and tighter constraint ranges will help to maintain local capture at each site, but will result in longer convergence times. If a site loses capture, as illustrated at point A in FIG. 15, the algorithm is reset only for the affected electrode while the remaining electrodes remain synchronized. Convergence continues with the affected electrode being resynchronized. Convergence is somewhat delayed by loss of a capture, but proceeds from the point when capture is regained. It should be understood, however, that capture must be maintained for a very large percentage of activation cycles in order for a convergence to occur.

A logical time to stop the pacing control and look for termination of the tachyarrhythmia is when convergence has occurred so that activation is simultaneous at all sites and the cycle length has been extended to some maximal value. Under these conditions, the maximum amount of cardiac tissue is captured and the mass available for sustaining fibrillation is at a minimum. A measure of convergence and cycle length is provided by the objective function $\Phi$ and the number of consecutive paces $(P_i)$ at each site. Pacing therapy should terminate when $P_i$ for every site becomes greater than a threshold $P_{thrsh}$ and the value of the objective function $\Phi$ falls below a critical threshold $\Phi_{min}$. This will reflect the condition under which pacing has been maintained for several intervals and pacing is nearly simultaneous at all sites. Although imminent termination of arrhythmia cannot be detected using this system, pacing will cease when the probability of termination is reasonably high. Failure to terminate the arrhythmia for a given attempt will result in reapplication of the multisite pacing therapy by the device. In case of atrial fibrillation, pacing therapy can be applied multiple times over periods of minutes and/or hours if necessary.

The embodiment discussed above in conjunction with the present invention is intended toward termination of atrial fibrillation by means of delivered cardiac pacing pulses. The device disclosed employs this mechanism as the only mechanism for termination of atrial fibrillation. However, the present method of termination of atrial fibrillation may also be employed in a device which also treats atrial fibrillation by means of cardioversion pulses, high frequency pacing, or other therapies. The invention may of course also be usefully employed in conjunction with a device which also treats atrial tachycardias using pacing level pulses and/or treats ventricular tachycardias and fibrillation using antitachycardia pacing pulses and/or defibrillation and cardioversion pulses.

Due to the calculations required in order to control pacing pulses at multiple sites according to the present invention, it is envisioned that the invention will most likely be embodied in microprocessor controlled devices. However, it is possible that the device might also be embodied in a device employing full custom digital circuitry, specifically adapted to perform the calculations required by the invention. Therefore, the above embodiment should be taken as exemplary, rather than limiting, with regard to the claims which follow.

In conjunction with the above disclosure, we claim:

1. A cardiac stimulator comprising:

a lead system carrying a plurality of stimulation electrodes adapted to be located at multiple sites adjacent tissue of a patient's heart;

stimulation pulse generators coupled to deliver stimulation pulses to said stimulation electrodes;

depolarization sensors responsive to depolarizations of cardiac tissues at said sites;

means responsive to said depolarization sensors for determining exitable gaps of tissue at said sites associated with depolarizations at said sites and associated with stimulation pulses delivered to said sites by said stimulation electrodes;

means for calculating stimulus pulse delivery times at variable delivery times within said determined exitable gaps at said sites to cause convergence of depolarization cycles at said sites over a series of delivered stimulation pulses; and control means for triggering said pulse generators to deliver stimulation pulses to said stimulation electrodes at said calculated times.

2. A stimulator according to claim 1 wherein said depolarization sensors comprise electrodes in addition to said stimulation electrodes.

3. A stimulator according to claim 1 or claim 2 comprising means for determining onset times of depolarizations at said sites and wherein said calculating means employs said onset times to calculate said variable delivery times within said exitable gaps.

4. A stimulator according to claim 3 wherein said calculating means comprises means for calculating said variable delivery times for all said plurality of stimulation electrodes responsive to each determined onset time of a depolarization at each said site.

5. A stimulator according to claim 1 or claim 2 comprising means for determining endpoint times of depolarizations at said sites and wherein said calculating means employs said determined endpoint times to calculate said variable delivery times within said exitable gaps.

6. A stimulator according to claim 5 wherein said calculating means comprises means for calculating said variable delivery times for all said plurality of stimulation electrodes responsive to each determined endpoint time of a depolarization at each said site.

7. A stimulator according to claim 1 or claim 2 wherein said calculating means comprises means for calculating said variable delivery times for all said plurality of stimulation electrodes responsive to each sensed depolarization.

8. A stimulator according to claim 1 or claim 2 wherein said calculating means comprises means for calculating said variable delivery times for all said plurality of stimulation electrodes responsive to each stimulation pulse delivered to said plurality of stimulation electrodes.

9. A method of cardiac stimulation, comprising:

locating a plurality of stimulation electrodes at multiple sites adjacent tissue of a patient's heart;

sensing depolarizations of cardiac tissues at said sites; and delivering stimulation pulses to said sites; and wherein said pulse delivering step comprises:

determining exitable gaps of tissue at said sites associated with depolarizations at said sites and associated with stimulation pulses delivered to said sites;

calculating stimulus pulse delivery times at variable delivery times within said determined exitable gaps at said sites to cause convergence of depolarization cycles at said sites over a series of delivered stimulation pulses; and delivering stimulation pulses to said stimulation electrodes at said calculated times.

10. A method according to claim 9 wherein said depolarization sensing step comprises sensing said depolarizations using electrodes in addition to said stimulation electrodes.

11. A method according to claim 9 or claim 10 further comprising the step of determining onset times of depolarizations at said sites and wherein said calculating step comprises employing said determined onset times to calculate said variable times within said exitable gaps.

12. A method according to claim 11 wherein said calculating step comprises calculating said variable delivery times for all said plurality of stimulation electrodes responsive to each determined onset time of a depolarization at each said site.

13. A method according to claim 9 or claim 10 further comprising the step of determining endpoints of depolarizations at said sites and wherein said calculating step comprises employing said determined endpoint times to calculate said variable times within said exitable gaps.

14. A method according to claim 13 wherein said calculating step comprises calculating said variable delivery times for all said plurality of stimulation electrodes responsive to each determined endpoint time of a depolarization at each said site.

15. A method according to claim 9 or claim 10 wherein said calculating step comprises calculating said variable delivery times for all said plurality of stimulation electrodes responsive to each sensed depolarization.

16. A method according to claim 9 or claim 10 wherein said calculating step comprises calculating said variable delivery times for all said plurality of stimulation electrodes responsive to each stimulation pulse delivered to said plurality of stimulation electrodes.

* * * * *